(12) United States Patent
Atkinson

(10) Patent No.: US 6,218,520 B1
(45) Date of Patent: *Apr. 17, 2001

(54) DNA SEQUENCES ENCODING HUMAN MEMBRANE COFACTOR PROTEIN (MCP)

(75) Inventor: John P. Atkinson, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 08/139,195

(22) Filed: Oct. 20, 1993

Related U.S. Application Data

(63) Continuation of application No. 07/948,350, filed on Sep. 21, 1992, now Pat. No. 5,514,787, which is a continuation of application No. 07/384,210, filed on Jul. 21, 1989, now abandoned.

(51) Int. Cl.[7] .............................. C07H 21/04; C12Q 1/68
(52) U.S. Cl. ......................... 536/23.1; 435/6; 536/24.31
(58) Field of Search ...................... 435/6, 810; 436/501; 536/22.1, 23.1, 24.31; 935/77, 78

(56) References Cited

PUBLICATIONS

*New England Biolabs Catalog* (publ. 1986/87 by New England Biolabs, Beverly, MA, USA) p. 60.*

Maniatis et al., Molecular Cloning, A Laboratory Manual (publ. 1982 by Cold Spring Harbor Labs., Cold Spring Harbor, NY, USA) pp. 387–389.*

* cited by examiner

*Primary Examiner*—Ardin H. Marschel
(74) *Attorney, Agent, or Firm*—Arnall Golden & Gregory, LLP

(57) ABSTRACT

Human membrane cofactor protein, a protein involved in regulation of complement activity, has been purified to homogeneity. The gene encoding this protein has been retrieved and permits deduction of the entire amino acid sequence and the recombinant production of this material. Pharmaceutical compositions in which MCP is the active ingredient for use in treating antoimmune diseases are also disclosed.

3 Claims, 3 Drawing Sheets

```
TCTGCTTTCCTCCGGAGAAATAACAGCGTCTTCCGCGCCGCGCATGGAGCCTCCCGGCCGCCGCGAGTGTCCC  73
                                         M  E  P  P  G  R  R  E  C  P   -25
                                        -34

TTTCCTTCCTGGCGCTTTCCTGGGTTGCTTCTGGCGGCCATGGTGTTGCTGCTGTACTCCTTCTCCGATGCC   145
 F  P  S  W  R  F  P  G  L  L  L  A  A  M  V  L  L  L  Y  S  F  S  D  A    1
                                                                      -1

TGTGAGGAGCCACCAACATTTGAAGCTATGGAGCTCATTGGTAAACCAAAACCCTACTATGAGATTGGTGAA   217
 C  E  E  P  P  T  F  E  A  M  E  L  I  G  K  P  K  P  Y  Y  E  I  G  E   24
+1

CCAGTAGATTATAAGTGTAAAAAAGGATACTTCTATATACCTCCTCTTGCCACCCATACTATTTGTGATCGG   289
 R  V  D  Y  K  C  K  K  G  Y  F  Y  I  P  P  L  A  T  H  T  I  C  D  R   48

AATCATACATGGCTACCTGTCTCAGATGACGCCTGTTATAGAGAAACATGTCCATATATACGGGATCCTTTA   361
 N  H  T  W  L  P  V  S  D  D  A  C  Y  R  E  T  C  P  Y  I  R  D  P  L   72

AATGGCCAAGCAGTCCCTGCAAATGGGACTTACGAGTTTGGTTATCAGATGCACTTTATTTGTAATGAGGGT   433
 N  G  Q  A  V  P  A  N  G  T  Y  E  F  G  Y  Q  M  H  F  I  C  N  E  G   96

TATTACTTAATTGGTGAAGAAATTCTATATTGTGAACTTAAAGGATCAGTAGCAATTTGGAGCGGTAAGCCC   505
 Y  Y  L  I  G  E  E  I  L  Y  C  E  L  K  G  S  V  A  I  W  S  G  K  P  120

CCAATATGTGAAAAGGTTTTGTGTACACCACCTCCAAAAATAAAAAATGGAAAACACACCTTAGTGAAGTA   577
 P  I  C  E  K  V  L  C  T  P  P  P  K  I  K  N  G  K  H  T  F  S  E  V  144

GAAGTATTTGAGTATCTTGATGCAGTAACTTATAGTTGTGATCCTGCACCTGGACCAGATCCATTTTCACTT   649
 E  V  F  E  Y  L  D  A  V  T  Y  S  C  D  P  A  P  G  P  D  P  F  S  L  168

ATTGGAGAGAGCACGATTTATTGTGGTGACAATTCAGTGTGGAGTCGTGCTGCTCCAGAGTGTAAAGTGGTC   721
 I  G  E  S  T  I  Y  C  G  D  N  S  V  W  S  R  A  A  P  E  C  K  V  V  192

AAATGTCGATTTCCAGTAGTCGAAAATGGAAAACAGATATCAGGATTTGGAAAAAAATTTTACTACAAAGCA   793
 K  C  R  F  P  V  V  E  N  G  K  Q  I  S  G  F  G  K  K  F  Y  Y  K  A  216

ACAGTTATGTTTGAATGCGATAAGGGTTTTTACCTCGATGGCAGCGACACAATTGTCTGTGACAGTAACAGT   865
 T  V  M  F  E  C  D  K  G  F  Y  L  D  G  S  D  T  I  V  C  D  S  N  S  240

ACTTGGGATCCCCCAGTTCCAAAGTGTCTTAAAGTGTCGACTTCTTCCACTACAAAATCTCCAGCGTCCAGT   937
 T  W  D  P  P  V  P  K  C  L  K  V  S  T  S  S  T  T  K  S  P  A  S  S  264

GCCTCAGGTCCTAGGCCTACTTACAAGCCTCCAGTCTCAAATTATCCAGGATATCCTAAACCTGAGGAAGGA  1009
 A  S  G  P  R  P  T  Y  K  P  P  V  S  N  Y  P  G  Y  P  K  P  E  E  G  288

ATACTTGACAGTTTGGATGTTTGGGTCATTGCTGTGATTGTTATTGCCCATAGTTGTTGGAGTTGCAGTAATT  1081
 I  L  D  S  L  D  V  W  V  I  A  V  I  V  I  A  I  V  V  G  V  A  V  I  312

TGTGTTGTCCCGTACAGATATCTTCAAAGGAGGAAGAAGAAAGGGAAAGCAGATGCTGGAGCTGAATATGCC  1153
 C  V  V  P  Y  R  Y  L  Q  R  R  K  K  G  K  A  D  G  G  A  E  Y  A  336

ACTTACCAGACTAAATCAACCACTCCAGCAGAGCAGAGAGGCTGAATAGATTCCACAACCTGGTTTGCCAGT  1225
 T  Y  Q  T  K  S  T  T  P  A  E  Q  R  G  *                              350

TCATCTTTTGACTCTATTAAAATCTTCAATAGTTGTTATTCTGTAGTTTCACTCTCATGAGTGCAACTGTGG  1297

CTTAGCTAATATTGCAATGTGGCTTGAATGTAGGTAGCATCCTTTGATGCTTCTTTGAAACTTGTATGAATT  1369

TGGGTATGAACAGATTGCCTGCTTTCCCTTAAATAACACTTAGATTTATTGGACCAGTCAGCACAGCATGCC  1441

TGGTTGTATTAAAGCAGGGATATGCTGTATTTTATAAAATTGGCAAAATTAGAGAAATATAGTTCACAATGA  1513

GATTATATTTTCTTTGTAAAAAAAAAAAAAAAA                                         1546
```

FIG. 1A

```
TCTGCTTCCTCCGGAGAATAACAGGTCTTCCGCGCCGCGCATGGAGCCTCCCGGCCGCCGCGAGTGTCCC    73
                                       M   E   P   P   G   R   R   E   C   P   -25
                                      -34

TTTCCTTCCTGGCGCTTCCCTGGGTTGCTCTGCTGTGTACTCCTTCTCCGATGCC              145
 F   P   S   W   R   F   P   G   L   L   L   A   A   M   V   L   L   L   Y   S   F   S   D   A    1
                                                                            -1

TGTGAGGAGCCACCAACATTTGAAGCTATGGAGCTCATTGGTAAACCAAAACCCTACTATGAGATTGGTGAA    217
 C   E   E   P   P   T   F   E   A   M   E   L   I   G   K   P   K   P   Y   Y   E   I   G   E    24
+1

CGAGTAGATTATAAGTGTAAAAAAGGATACTTCTATATACCCTCCTCTTGCCACCATACTATTTGTGATCGG    289
 R   V   D   Y   K   C   K   K   G   Y   F   Y   I   P   P   L   A   T   H   T   I   C   D   R    48

AATCATACATGGCTACCTGTCTCAGATGACGCCTGTTATAGAGAAACATGTCCATATATACGGGATCCTTTA    361
 N   H   T   W   L   P   V   S   D   D   A   C   Y   R   E   T   C   P   Y   I   R   D   P   L    72

AATGGCCAAGCAGTCCCCTGCAAATGGGACTTACGAGTTTGGTTATCAGATGCACTTTATTTGTAATGAGGGT    433
 N   G   Q   A   V   P   A   N   G   T   Y   E   F   G   Y   Q   M   H   F   I   C   N   E   G    96

TATTACTTAATTGGTGAAGAAATTCTATATTGTGAACTTAAAGGATCAGTAGCAATTTGGAGCGGTAAGCCC    505
 Y   Y   L   I   G   E   E   I   L   Y   C   E   L   K   G   S   V   A   I   W   S   G   K   P    120

CCAATATGTGAAAAGGTTTTGTGTACACCACCTCCAAAAATAAAAATGGAAAACACACCTTTAGTGAAGTA    577
 P   I   C   E   K   V   L   C   T   P   P   P   K   I   K   N   G   K   H   T   F   S   E   V    144

GAAGTATTTGAGTATCTTGATGCAGTAACTTATAGTTGTGATCCTGCACCTGACCAGATCCATTTTCACTT    649
 E   V   F   E   Y   L   D   A   V   T   Y   S   C   D   P   A   P   G   P   D   D   P   F   S   L    168
```

FIG. 1B

```
ATTGGAGAGAGCACGATTTATTGTGGTGACAATTCAGTGTGGAGTCGTGCTGCTCCAGAGTGTAAAGTGGTC  721
 I  G  E  S  T  I  Y  C  G  D  N  S  V  W  S  R  A  A  P  E  C  K  V  V   192

AAATGTCGATTTCCAGTAGTCGAAAATGGAAAACAGATATCAGGATTTGGAAAAAAATTTACTACAAAGCA  793
 K  C  R  F  P  V  V  E  N  G  K  Q  I  S  G  F  G  K  K  F  Y  Y  K  A   216

ACAGTTATGTTTGAATGCGATAAGGGTTTTTACCTCGATGGCAGGCGACACAATTGTCTGTGACAGTAACAGT  865
 T  V  M  F  E  C  D  K  G  F  Y  L  D  G  S  D  T  I  V  C  D  S  N  S   240

ACTTGGGATCCCCCAGTTCCAAAGTGTCTTAAAGTGTCGACTTCTTCCACTACAAAATCTCCAGCCGTCCAGT  937
 T  W  D  P  P  V  P  K  C  L  K  V  S  T  S  S  T  T  K  S  P  A  S  S   264

GCCTCAGGTCCTAGGCCTACTTACAAGCCCTCCAGTCTCAAATTATCCAGGATATCCTAAACCTGAGGAAGGA 1009
 A  S  G  P  R  P  T  Y  K  P  P  V  S  N  Y  P  G  Y  P  K  P  E  E  G   288

ATACTTGACAGTTTGGATGTTTGGGTCATTGCTGTGATTGTTATTGCCATAGTTGTTGGAGTTGCAGTAATT 1081
 I  L  D  S  L  D  V  W  V  I  A  V  I  V  I  A  I  V  V  G  V  A  V  I   312

TGTGTTGTCCCGTACAGATATCTTCAAAGGAGGAAGAAAGAAAGGGAAAGCAGATGGTGGAGCTGAATATGCC 1153
 C  V  V  P  Y  R  Y  L  Q  R  R  K  K  K  G  K  A  D  G  G  A  E  Y  A   336

ACTTACCAGACTAAATCAACCACTCCAGCAGAGCAGAGAGGCTGAATAGAGATTCCACAACCTGGTTTGCCAGT 1225
 T  Y  Q  T  K  S  T  T  P  A  E  Q  R  G  *                                350

TCATCTTTTGACTCTCTATTAAAATCTTCAATAGTTGTTATTCTGTAGTTTCACTCTCATGAGTGCAACTGTGG 1297
```

FIG. 1C

```
CTTAGCTAATATTGCAAATGTGGCTTGAATGTAGGTAGCATCCTTTGATGCTTCTTTGAAACTTGTATGAATT 1369
TGGGTATGAACAGATTGCCTGCTTTCCCTTAAATAACACTTAGATTTATTGGACCAGTCAGCACAGCATGCC 1441
TGGTTGTATTAAAGCAGGGATATGCTGTATTTTATAAAATTGGCAAAATTAGAGAAAATATAGTTCAAATGA 1513
AATTATATTTCTTTGTAAAAAAAAAAAAAAA 1546
```

DNA SEQUENCES ENCODING HUMAN MEMBRANE COFACTOR PROTEIN (MCP)

This is a continuation of U.S. Ser. No. 07/948,350 filed Sep. 21, 1992, now U.S. Pat. No. 5,514,787; by John P. Atkinson entitled "Recombinantly Produced Human Membrane Cofactor Protein (MCP)," which is a continuation of U.S. Ser. No. 07/384,210 filed Jul. 21, 1989 now abandoned, by John P. Atkinson entitled "Recombinantly Produced Human Membrane Cofactor Protein (MCP)."

TECHNICAL FIELD

The invention is related to human therapeutics and regulation of the complement cascade. More specifically, it concerns the recombinant production of human membrane cofactor protein (MCP) (Sequence ID No. 2) which is an important factor in the regulation of complement cascade.

BACKGROUND ART

The complement system is capable of tissue and cell destruction and is therefore a major element of the defense system against invasion by foreign tissue. However, control of this system is necessary in order to prevent destruction of autologous cells. A large number of proteins. which are involved in control of the complement cascade have been described.

Most relevant to the present invention is the group which controls the C3 convertase stage of the cascade and binds to fragments of either C3 or C4 or both. This group includes serum proteins such as C4-binding protein and factor H and membrane proteins such as C3b receptor, C3d/Epstein-Barr virus receptor, decay-accelerating factor (DAF), and the protein of the invention, membrane cofactor protein (MCP) (Sequence ID No. 2). Reviews of these various factors and their role in complement cascade regulation can be found in Holers, B. M., et al., *Immunol Today* (1985) 6:188; Ross, G. D., et al., *Adv Immunol* (1985) 37:217; Atkinson, J. P., et al., *Immunol Today* (1987) 8:212.

Much is known concerning these regulatory proteins, except for MCP. They are each composed of multiple repeats of an approximately 60-amino acid consensus sequence composed of conserved cys, pro, gly, trp, leu/ile/val, and tyr/phe residues (Reid, K., et al., *Immunol Today* (1986) 7:230). The genes encoding these proteins have been localized to the long arm of human chromosome 1, band lq32 and form a multigene family designated the regulator of complement activation (RCA) gene cluster. As will be shown below, MCP is also a member of this family.

A member of this family particularly related to the MCP (Sequence ID No. 2) of the invention is the decay-accelerating factor (DAF) which was identified on human platelets by Yu, G.H., et al., *J Clin Invest* (1986) 78:494–501. DAF is present on virtually all peripheral blood cells, including erythrocytes, granulocytes, T and B lymphocytes, monocytes, and platelets; in addition, soluble forms of DAF have been found in extracellular fluids and tissue culture supernatants. The gene encoding DAF has been cloned and sequenced (by Medof, M. E., et al., *Proc Natl Acad Sci USA* (1987) 84:2007–2011; and by Caras, I. W., et al., *Science* (1987) 238:1280–1283). It has been shown that the membrane and soluble secreted forms of DAF result from differential splicing of the mRNA encoding these proteins with the soluble form having a longer C-terminus, but a C-terminus which lacks the membrane binding region associated with the membrane DAF, as described in PCT application W089/01041.

MCP was initially identified by iC3/C3b affinity chromatography on surface-labeled peripheral blood cells and designated gp45–70 to describe the range of $M_r$ obtained on SDS-PAGE (Cole, J. L., et al., *Proc Natl Acad Sci USA* (1985) 82:859). MCP was partially purified from the human mononuclear cell lines and shown to have a cofactor activity but no decay accelerating function (Seya, T. J., et al., *J Exp Med* (1986) 163:837). MCP is absent from erythrocytes, but present as a membrane-bound protein on human T and B lymphocytes, granulocytes, monocytes, platelets, endothelial cells, epithelial cells, and fibroblasts; on most of these cells it occurs in polymorphic forms of molecular weight 63 kd and 58 kd, as determined by SDS-PAGE. These appear to result from a two allelic system encoding MCP (Ballard, L., et al., *J Immunol* (1987) 138:3850–3855). The MCP found by immunoprecipitation on the membranes of granulocytes appears, however, not to exhibit this polymorphism (Seya, T., et al., *Eur J Immunol* (1988) 18:1289–1294). The occurrence of MCP on a wide range of host cells is consistent with a role in protecting host cells from damage by complement (Seya, T. L., et al., *Complement* (1987) 4:225).

The previously purified MCP has been utilized to prepare a polyclonal rabbit antiserum monospecific for this protein. The antisera were raised in rats by repetitive injections of MCP purified as described by Seya, T., et al., *J Exp Med* (1986) (supra), in complete Freund's adjuvant. These antisera have been used to identify MCP in extracts from various membranes.

The present invention provides a more highly purified form of this protein and the capacity to produce it recombinantly, thus providing practical quantities for therapeutic use.

DISCLOSURE OF THE INVENTION

Human membrane cofactor protein (MCP)(Sequence ID No. 2) is a significant protector of host tissue from autologous destruction by the complement system. Practical quantities of this protein and antibodies specifically immunoreactive with it are made available by recombinant production of human MCP.

Accordingly, in one aspect, the invention is directed to purified and isolated human MCP and to human MCP produced recombinantly. In other aspects, the invention is directed to recombinant materials and methods which result in the manufacture of useful quantities of this protein. Also an aspect of the invention are antibodies immunoreactive with the protein which are useful in diagnosis of disorders associated with reduced or elevated amounts of MCP. Further, the invention includes genetic probes useful in detecting polymorphisms of the MCP-encoding gene (Sequence ID No. 1), and in obtaining DNA encoding corresponding MCP in other species.

In still further aspects, the invention is directed to pharmaceutical compositions containing the MCP of the invention and to methods of treating or ameliorating inflammatory and autoimmune conditions mediated by an excess or misdirection of complement activity.

In still another aspect, the invention is directed to methods to diagnose abnormalities in the immune system, specifically the presence or absence of autoimmune disease by assessing the levels of MCP present on peripheral blood cells and to a method to predict the probability of recurrent miscarriage by testing elevated levels of MCP in the placenta.

BRIEF DESCRIPTION OF THE DRAWINGS

FIGS. 1A, 1B and 1C shows the nucleotide sequence ID No. 1 and deduced amino acid sequence ID No. 2 of human MCP.

MODES OF CARRYING OUT THE INVENTION

As used herein, human MCP refers to a protein which shows complement-inhibitory activity according to standard hemolysis assays described below, has cofactor activity according to the assay of Turner, J. R., et al., Masters Thesis, Washington U., St. Louis, Mo. (1984), ; is free of decay-accelerating function as assayed according to Hoffmann, E. M., *Immunochemistry* (1969) 6:405–419, and has an amino acid sequence referenced to that shown as amino acids 1–350 in FIGS. 1A, 1B and 1C Sequence ID No. 2 herein. By "referenced to" is meant that the protein contains the same amino acid sequence as that shown, is encoded by a DNA which represents an allelic variant of the DNA encoding the amino acid sequence shown, or has an amino acid sequence which has deletions, insertions, and/or substitutions of individual or multiple amino acid residues which do not alter the qualitative pattern of activity described. For example, and specifically included among amino acid sequences referenced to that shown in FIGS. 1A, 1B and 1C, are those in which the membrane binding region indicated by the boldface underline in the figure is deleted, along with allelic variants of the remaining portion. The protein in soluble form is thus specifically included.

With respect to deletions and insertions, preferred are those wherein only one, two or a small number of amino acid residues in the first 238 amino acid sequence of the mature protein, before the arrow at residue 239, are inserted or deleted. More substantial alterations can be made downstream of this arrow. Preferred substitutions are those which are conservative—i.e., hydrophobic amino acids substituted for hydrophobic amino acids, positively charged amino acids for positively charged, etc. Thus, preferred substitutions are glu for asp and vice versa, lys for his for arg and permutations thereof; substitutions among the group ile, val, met, and leu; substitutions among the group gly, ala, ser and cys; and substitutions among the group trp, tyr, and phe.

As is understood in the art, the protein may exist in a variety of ionization states depending on the pH conditions in which it is prepared. Thus, the MCP protein may exist in the salt form (salts formed from bases as to the carboxyl groups or acid addition salts as to the amino groups). Furthermore, the protein may be derivatized in various ways, including glycosylation, acylation, sulfation, and the like. It is believed that as glycosylation is a post-translational process, the glycosylation pattern is dependent on the nature of the cell in which the protein is produced. Differences in glycosylation pattern are particularly understood to be relevant to the present case. For example, it has been shown that the dimorphic character of the MCP extracted from membranes of various peripheral blood cells is in part accounted for by the difference in quantity of sialic acid in the two formns (Ballard, L. L., et al., *J Immunol* (1988) 141:3923–3929), incorporated herein by reference). According to this disclosure, the two forms of MCP derived from human mononuclear cells and cell lines are shown to have three of four peptides obtained by peptide mapping which are identical, whereas the largest partially digested peptide is different, and the difference in sialic residues accounts for most of the molecular weight difference between the two species.

As shown in FIGS. 1A, 1B and 1C, the DNA encoding the human MCP (Sequence ID No. 1) from the human T cell line HSB2 is now available in the art. DNA encoding this particular embodiment can be obtained as described in the Examples below or, preferably, can be synthesized de novo using known techniques. Alternatively, partial cloned sequences can be ligated to synthetic portions. Alterations in the sequence shown in FIGS. 1A, 1B and 1C can be incorporated into the de novo synthesis or can be obtained from previously synthesized or cloned DNA using site-directed mutagenesis, as is known in the art per se. Provision of and disclosure of the complete amino acid sequence for the protein acting as a cofactor, as shown in residues 1–238 of FIG. 1, permit synthesis of DNAs encoding not only this sequence, with or without the membrane-attaching portion thereof, but also alternate forms which are referenced to the protein shown as 1–350 in FIGS. 1A, 1B and 1C.

The DNA is preferably provided with linkers for ligation into cloning and expression vectors. Techniques for preparation of such vectors are well understood in the art. The DNA encoding the desired MCP is ligated in operable linkage with control sequences, including promoters, upstream enhancers, termination sequences, and so forth, depending on the nature of the intended recombinant host cells. Technology is currently available for expression of heterologous genes, including MCP in its various forms, in a variety of hosts, including procaryotic hosts and various eucaryotes, including yeasts, mammalian or avian or insect cells, and plant cells. The choice of control sequences and markers in the expression vectors is selected appropriately to these hosts.

For example, in procaryotic hosts, various promoters, including inducible promoters such as the trp promoter and lambda phage $P_L$ promoter can be employed. Hybrid promoters such as the tac promoter, which contains the trp polymerase binding region in combination with the lactose operator, can be used. Suitable markers are generally those related to antibiotic resistance. On the other hand, in mammalian cell cultures, commonly used promoters are virally derived, such as the early and late SV40 promoters, adenovirus promoters, metallothionein-II promoter, and the like. Some of these promoters are also capable of being regulated by conditions-in the medium, such as the metallothionein-II promoter, which is regulated by glucocorticoids or heavy metals. These promoter systems are compatible with typical mammalian hosts, most commonly Chinese hamster ovary (CHO) cells.

Another commonly employed system is the baculovirus expression system compatible with insect cells. Plant cells, used in conjunction with, for example, the nopaline synthetase promoter, and yeast cells, used in conjunction with promoters associated with enzymes important in the glycolytic pathway, can also be employed. A number of suitable expression systems can be found in appropriate chapters in "Current Protocols in Molecular Biology," Ausubel, F. M., et al., eds., published by Wiley Interscience, latest edition.

Although greatly more laborious, the desired MCP peptide, now that its amino acid sequence has been elucidated by sequencing of the gene, could be synthesized by standard amino acid coupling techniques to obtain smaller peptides which could then be coupled using known techniques.

Regardless of the mode of preparation, whether recombinant or synthetic (or, indeed, by isolation from nature sources), the MCP is purified using techniques analogous to those described by Ballard et al., *J Immunol* (1988) (supra).

The purified protein is then formulated for administration using techniques known generally to treat or alleviate the symptoms of diseases and conditions characterized by excessive complement activity. Such diseases include autoimmune diseases, for example, rheumatoid arthritis, systemic lupus erythematosis, thyroiditis, myasthenia gravis, multiple sclerosis; and other diseases which are characterized by inflammation, such as arteritis of serum sickness, proteinuria in acute nephrotoxic nephritis, kidney inflammation, including glomerulitis, and insulin-dependent diabetes myelitis.

The MCP is generally formulated for injection, either systemically or directly to the tissues affected. Suitable formulations can be found, for example, in *Remington's Pharmaceutical Sciences* (1985), Mack Publishing Company, Easton, Pa., latest edition. For injection, the protein is dissolved or suspended in liquid medium, for example, Hank's solution, Ringer's solution, dextrose solution, and various buffers. Additional excipients such as stabilizers can also be employed.

Besides injection, the peptides of the invention can be administered systemically, via suppository, oral administration, transmucosal administration, including intranasal sprays, and by slow release formulations. Additional formulation techniques include encapsulation formulations, such as liposomes.

Finally, the peptides of the invention can be conjugated to target-directing ligands to carry them to the site of desired bioactivity. Such ligands can include, most commonly, immunoglobulins or their fragments and ligands specific for cell-associated receptors. Targeted forms of the MCP are particularly useful in treating allograft rejections by targeting the foreign tissue.

In addition to utility as a therapeutic, the MCP can be used to raise polyclonal antisera or to produce cells which can be fused to immortalizing partners to obtain sources of monoclonal antibodies specific for MCP. These antibodies are useful as a passive therapeutic to treat diseases which are characterized by low complement activity, or to remedy deficiencies in the complement system, and also to raise antiidiotypic antibodies which are, in turn, therapeutically useful. The antibodies of the invention are also useful diagnostic tools for assay of MCP levels on peripheral blood cells or other normally MCP-bearing cells using standard immunoassay techniques.

As described in *Molecular Cloning. A Laboratory Manual*, Sambrook, et al., (Cold Spring Harbor Laboratory Press, 1989), sequences of at least seventeen consecutive nucleotides of the cDNA of the invention, homologous to that shown in FIGS. 1A, 1B and 1C, is also useful as a probe to recover analogous MCP-encoding DNAs in a variety of species, in addition to human. This cDNA or its homologs can be used diagnostically as a probe to detect elevated levels of MCP in placental tissue; these elevated levels are predictive of propensity for miscarriages in future pregnancies.

The following examples are intended to illustrate but not limit the invention.

EXAMPLE 1

Preparation of Purified Human MCP

The procedure of Seya, T., et al., *J Exp Med* (1986) 163:837, cited above, and incorporated herein by reference was employed. The protein was purified from the T cell line HSB2 by solubilization in NP-40 followed by sequential chromatography on chromatofocusing, hydroxyapatite, C3 (methylamine) Sepharose, and Mono Q columns. Approximately 20 ug of partially purified protein thus obtained was subjected to 10% SDS-PAGE and the 63 kd Mr band was electroeluted and electrodialyzed according to the procedure of Hunkapiller, M. W., et al., Meth Enzymol (1983) 91:227. The resulting protein was homogeneous according to the criteria of SDS-PAGE and HPLC.

EXAMPLE 2

Recovery of cDNA-encoding MCP

The monocyte U937 cell line was used as a source of mRNA. This was prepared using standard procedures including guanidinium isothiocyanate/CsCl extraction as described by Chirgwin, J. M., et al., Biochemistry (1979) 18:5294, followed by isolation of mRNA on oligo(dT)-cellulose chromatography (Aviv, H., et al., *Proc Natl Acad Sci USA* (1972) 69:1408). The cDNA library was prepared from 5 ug of the isolated mRNA by the method of Gubler, U., et al., Gene (1983) 25:263 and cDNA inserts of greater than 1 kb were ligated into lambda-gt10 arms, packaged and plated on C600 hflA *E. coli* to obtain $2 \times 10^6$ recombinants. The cDNA library was probed with a $^{32}$p-labeled 64 degenerate 17-mer antisense oligonucleotide probe based on residues 7–12 of the MCP protein as determined by amino acid sequencing of the purified protein of Example 1. The 17-mer encoded the sequence Phe-Glu-Ala-Met-Glu-Leu (amino acids 41–46 of Sequence ID No. 2). The library was probed on plaque lifts on nitrocellulose filters wherein the filters the filters were hybridized overnight at 37° C. in 6×SSC (1×SSC—0.15 M sodium chloride/0.015 M sodium citrate)/ 5×Denhardt's solution (1×Denhardt's =0.02% BSA/0.02% Ficoll/0.02% polyvinylpyrrolidone)/0.05 M sodium phosphate, pH 6.8, containing 100 ug sonicated herring sperm DNA and 5×105 cpm labeled probe per mil. The filters were washed two times for 30 min with 2×SSC/0.1% SDS at room temperature.

The plaques yielding positive signals in duplicate were plaque purified using standard methods.

The positive plaques were cloned into pUC-19 and sequenced using the standard dideoxy sequencing method. One clone which contained a 1.5 kb insert was sequenced with the results shown in FIGS. 1A, 1B and 1C.

As shown in FIGS. 1A, 1B and 1C, the cDNA contains an open reading frame encoding 384 amino acids. The first 34 amino acids are a typical structure for a signal peptide; the succeeding 24 amino acids match the N-terminal protein sequence determined by Edman degradation of the protein in Example 1. The putative protein without signal of 39 kd agrees with the size of the MCP precursor detected in biosynthetic studies by Ballard, L. L., et al., Fed Proc (1987) 46:773. It will be seen that there are 3 N-linked glycosylation sites and multiple potential O-linked glycosylation sites in the ser/thr-rich region (12/25 residues) between amino acids 253–277, consistent with the oligosaccharide structure of MCP as determined by Ballard et al., supra. Hydrophobicity analysis according to Hopp, T. P., et al., *Proc Natl Acad Sci USA* (1981) 78:3824 show a 23-amino acid region typical for a transmembrane hydro-phobic domain at amino acids 295–317, followed by a 33-amino acid region corresponding to a cytoplasmic tail. The untranslated downstream region is consistent with a polyadenylation site.

However, the bulk of the protein at the N-terminus consists of 4 contiguous domains of about 60 amino acids which match the consensus sequence found in the multigene family of complement regulatory proteins. These 4-domains show 18–35% amino acid sequence homology to each other (29–44% if conservative amino acid sequences are allowed) similar to the degree of homology in other members of the family.

What is claimed is:

1. A DNA probe for human membrane cofactor protein hybridizing to and effective to detect the DNA sequence in Sequence Listing I.D. No. 1 when hybridized overnight at 37° C. in 6×(0.15 M sodium chloride/0.015 M sodium citrate), 5×(0.02% BSA/0.02% Ficoll/0.02% polyvinylpyrrolidonel/0.05 M sodium phosphate, pH 6.8, in the presence of sonicated herring sperm DNA, followed by washing two times for thirty minutes with 2×0.15 M sodium chloride/0.015 M sodium citrate plus 0.1% SDS at room temperature.

2. The DNA probe of claim 1 wherein the probe has a sequence in Sequence Listing I.D. No. 1.

3. The DNA probe of claim 1 wherein the probe is at least seventeen nucleotides in length.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1545 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human t-Cell Line HSB2

(xi) SEQUENCE DESCRIPTION: SEQ ID NO:1:

```
TCTGCTTTCC TCCGGAGAAA TAACAGCGTC TTCCGCGCCG CGCATGGAGC CTCCCGGCCG      60

CCGCGAGTGT CCCTTTCCTT CCTGGCGCTT TCCTGGGTTG CTTCTGGCGG CCATGGTGTT     120

GCTGCTGTAC TCCTTCTCCG ATGCCTGTGA GGAGCCACAA CCATTTGAAG CTATGGAGCT     180

CATTGGTAAA CCAAAACCCT ACTATGAGAT TGGTGAACGA GTAGATTATA AGTGTAAAAA     240

AGGATACTTC TATATACCTC CTCTTGCCAC CCATACTATT TGTGATCGGA ATCATACATG     300

GCTACCTGTC TCAGATGACG CCTGTTATAG AGAAACATGT CCATATATAC GGGATCCTTT     360

AAATGGCCAA GCAGTCCCTG CAAATGGGAC TTACGAGTTT GGTTATCAGA TGCACTTTAT     420

TTGTAATGAG GGTTATTACT TAATTGGTGA AGAAATTCTA TATTGTGAAC TTAAAGGATC     480

AGTAGCAATT TGGAGCGGTA AGCCCCCAAT ATGTGAAAAG GTTTTGTGTA CACCACCTCC     540

AAAAATAAAA AATGGAAAAC ACACCTTTAG TGAAGTAGAA GTATTTGAGT ATCTTGATGC     600

AGTAACTTAT AGTTGTGATC CTGCACCTGG ACCAGATCCA TTTTCACTTA TTGGAGAGAG     660

CACGATTTAT TGTGGTGACA ATTCAGTGTG GAGTCGTGCT GCTCCAGAGT GTAAAGTGGT     720

CAAATGTCGA TTTCCAGTAG TCGAAAATGG AAAACAGATA TCAGGATTTG GAAAAAAATT     780

TTACTACAAA GCAACAGTTA TGTTTGAATG CGATAAGGGT TTTTACCTCG ATGGCAGCGA     840

CACAATTGTC TGTGACAGTA ACAGTACTTG GGATCCCCCA GTTCAAAGTG TCTTAAAGTG     900

TCGACTTCTT CCACTACAAA ATCTCCAGCG TCCAGTGCCT CAGGTCCTAG GCCTACTTAC     960

AAGCCTCCAG TCTCAAATTA TCCAGGATAT CCTAAACCTG AGGAAGGAAT ACTTGACAGT    1020

TTGGATGTTT GGGTCATTGC TGTGATTGTT ATTGCCATAG TTGTTGGAGT TGCAGTAATT    1080

TGTGTTGTCC CGTACAGATA TCTTCAAAGG AGGAAGAAGA AAGGGAAAGC AGATGGTGGA    1140

GCTGAATATG CCACTTACCA GACTAAATCA ACCACTCCAG CAGAGCAGAG AGGCTGAATA    1200

GATTCCACAA CCTGGTTTGC CAGTTCATCT TTTGACTCTA TTAAAATCTT CAATAGTTGT    1260

TATTCTGTAG TTTCACTCTC ATGAGTGCAA CTGTGGCTTA GCTAATATTG CAATGTGGCT    1320

TGAATGTAGG TAGCATCCTT TGATGCTTCT TTGAAACTTG TATGAATTTG GGTATGAACA    1380

GATTGCCTGC TTTCCCTTAA ATAACACTTA GATTTATTGG ACCAGTCAGC ACAGCATGCC    1440

TGGTTGTATT AAAGCAGGGA TATGCTGTAT TTTATAAAAT TGGCAAAATT AGAGAAATAT    1500

AGTTCACAAT GAAATTATAT TTTCTTTGTA AAAAAAAAAA AAAA                     1545
```

(2) INFORMATION FOR SEQ ID NO:2:

(i) SEQUENCE CHARACTERISTICS:
        (A) LENGTH: 384 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Human Membrane CoFactor Protein (MCP)

(xi) SEQUENCE DESCRIPTION: SEQ ID NO:2:

```
Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
            35                  40                  45

Lys Pro Lys Pro Tyr Tyr Glu Ile Gly Glu Arg Val Asp Tyr Lys Cys
        50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Ala Cys Tyr Arg
                85                  90                  95

Glu Thr Cys Pro Tyr Ile Arg Asp Pro Leu Asn Gly Gln Ala Val Pro
                100                 105                 110

Ala Asn Gly Thr Tyr Glu Phe Gly Tyr Gln Met His Phe Ile Cys Asn
            115                 120                 125

Glu Gly Tyr Tyr Leu Ile Gly Glu Glu Ile Leu Tyr Cys Glu Leu Lys
        130                 135                 140

Gly Ser Val Ala Ile Trp Ser Gly Lys Pro Pro Ile Cys Glu Lys Val
145                 150                 155                 160

Leu Cys Thr Pro Pro Pro Lys Ile Lys Asn Gly Lys His Thr Phe Ser
                165                 170                 175

Glu Val Glu Val Phe Glu Tyr Leu Asp Ala Val Thr Tyr Ser Cys Asp
                180                 185                 190

Pro Ala Pro Gly Pro Asp Pro Phe Ser Leu Ile Gly Glu Ser Thr Ile
            195                 200                 205

Tyr Cys Gly Asp Asn Ser Val Trp Ser Arg Ala Ala Pro Glu Cys Lys
        210                 215                 220

Val Val Lys Cys Arg Gly Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
                260                 265                 270

Asn Ser Thr Trp Asp Pro Pro Val Pro Lys Cys Leu Lys Val Ser Thr
            275                 280                 285

Ser Ser Thr Thr Lys Ser Pro Ala Ser Ser Ala Ser Gly Pro Arg Pro
        290                 295                 300
```

-continued

```
Thr Tyr Lys Pro Pro Val Ser Asn Tyr Pro Gly Tyr Pro Lys Pro Glu
305             310             315             320

Glu Gly Ile Leu Asp Ser Leu Asp Val Trp Val Ile Ala Val Ile Val
            325             330             335

Ile Ala Ile Val Val Gly Val Ala Val Ile Cys Val Val Pro Tyr Arg
            340             345             350

Tyr Leu Gln Arg Arg Lys Lys Lys Gly Lys Ala Asp Gly Gly Ala Glu
            355             360             365

Tyr Ala Thr Tyr Gln Thr Lys Ser Thr Thr Pro Ala Glu Gln Arg Gly
            370             375             380
```